United States Patent [19]

Andrychuk

[11] Patent Number: 5,424,830
[45] Date of Patent: Jun. 13, 1995

[54] METHOD AND APPARATUS FOR DETERMINING THE FACET ANGLES OF A GEMSTONE

[76] Inventor: Dmetro Andrychuk, 422 Terrace Dr., Richardson, Tex. 75081

[21] Appl. No.: 322,575

[22] Filed: Oct. 13, 1994

[51] Int. Cl.$^6$ .................... G01N 21/87; G01B 11/26
[52] U.S. Cl. ........................ 356/30; 356/154
[58] Field of Search ........................ 356/30, 154

[56] References Cited

U.S. PATENT DOCUMENTS

| | | | |
|---|---|---|---|
| 1,700,496 | 1/1929 | Heitzler | 356/30 |
| 1,700,497 | 1/1929 | Heitzler | 356/30 |
| 1,799,604 | 4/1931 | Read | 356/30 |
| 3,751,162 | 8/1973 | Long | 356/30 |
| 3,782,836 | 1/1974 | Fey et al. | 356/237 |
| 3,858,979 | 1/1975 | Elbe | 356/30 |
| 4,065,211 | 12/1977 | Vig | 356/152 |

FOREIGN PATENT DOCUMENTS 2034914  6/1980  United Kingdom ............. 356/30

Primary Examiner—F. L. Evans
Attorney, Agent, or Firm—Ross, Clapp, Korn & Montgomery

[57] ABSTRACT

A method and apparatus for determining the facet angles of a gemstone includes structure for rotatably mounting a gemstone along the optical axis of the gemstone. A collimated beam of light is directed toward a facet of the gemstone, such that the facet reflects light. A scale is mounted parallel to and spaced apart from the gemstone optical axis. The scale includes indicia indicating angular measurements, such that the facet reflected light impinges on the scale. The location of the facet reflected light on the scale indicia indicates the angle of the facet.

2 Claims, 1 Drawing Sheet

METHOD AND APPARATUS FOR DETERMINING THE FACET ANGLES OF A GEMSTONE

TECHNICAL FIELD OF THE INVENTION

The present invention relates to measuring instrumentation, and more particularly to a method and apparatus for determining the facet angles of gemstones.

BACKGROUND OF THE INVENTION

Faceted gemstones include a transparent material cut into round, rectangular, oval, square or marquis shapes and consist of facets cut at various angles both on the crown and pavilion. The facets are disposed around the gem and over the entire gemstone surface. The angles of the facets are determined with respect to the optical axis of the gem, and determine the performance of the gem as regard to the gem's reflected and refracted light that is incident on the gem.

When the gem is mounted in a ring, pendant, or pin and is worn by the user, the facets may be scratched, chipped, and marred. Additionally, the gem, during shipment from the gem supplier to the final jeweler may be damaged. When damaged, the gem must then have the facets repolished to restore the gem to its original and clean and polished state.

Since the angles of the gem facets are unknown to the jeweler supplying the stone, or the owner of the stone, the angles of the gem facets must be determined in order to allow the gem cutter to restore the gem by repolishing facets to their original angle, thereby repairing damaged gems into their original polished facets at the original angles.

A need has thus developed for a measuring device in order to determine the facet angles of a gemstone.

SUMMARY OF THE INVENTION

In accordance with the present invention, a method and apparatus for determining the facet angles of a gemstone is provided. The apparatus includes structure for rotatably mounting a gemstone along the optical axis of the gemstone. A collimated beam of light is directed toward a facet of the gemstone, such that the facet reflects light. A scale is mounted parallel to and spaced apart from the gemstone optical axis. The scale includes indicia indicating angular measurements, such that the facet reflected light impinges on the scale. The location of the facet reflected light on the scale indicia indicates the angle of the facet.

BRIEF DESCRIPTION OF THE DRAWINGS

For a more complete understanding of the present invention and for further advantages thereof, reference is now made to the following Description of the Preferred Embodiments taken in conjunction with the accompanying Drawings in which.

DESCRIPTION OF THE PREFERRED EMBODIMENTS

Figure 1:
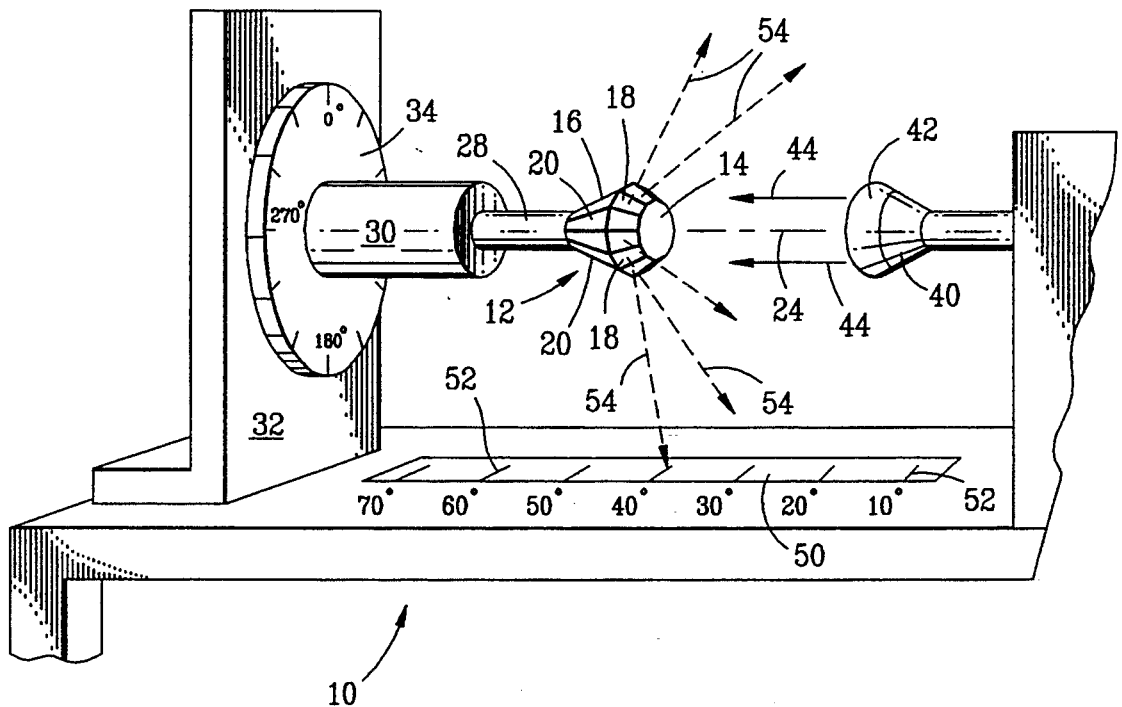
FIG. 1 is a diagrammatic illustration of the present apparatus.

Referring to FIG. 1, an apparatus for determining the facet angles of a gemstone is illustrated, and is generally identified by the numeral 10. Apparatus 10 is utilized for measuring the facet angles of a gemstone, generally identified by the numeral 12. Gemstone 12 includes a crown 14 and a pavilion 16. Disposed along the surface of crown 14 are facets 18. Disposed along the surface of pavilion 16 are facets 20.

Gemstone 12 is mounted along its optical axis 24 in a dop 28. Dop 28 is received by a quill 30 of a faceting machine 32. Quill 30 is rotatably mounted to faceting machine 32 for rotatably moving gemstone 12. Faceting machine 32 includes an index gear 34 that permits reading the rotational position of gemstone 12 with respect to optical axis 24. Although a faceting machine 32 is shown in FIG. 1 for use with the present apparatus 10, any device for rotatably mounting gemstone 12 for rotation may be utilized with the present invention.

Mounted along the optical axis 24 of gemstone 12 is an illumination source 40 which may comprise, for example, an incandescent source or a light emitting diode. The light generated by source 40 passes through an optical lens 42 for directing the light into a collimated or parallel beam 44. Light beam 44 impinges upon gemstone 12, and particularly onto facets 18.

Disposed parallel to the optical axis 24 and below gemstone 12 is a scale 50. Scale 50 includes indicia 52 which represent angular measurements determined in accordance with the present invention.

Light beam 44 directed to facets 18, is reflected at various angles, and the reflection impinges onto scale 50. For the particular facet under investigation, which is identified by the degree on index gear 34, a reflected light ray is generated, as indicated by rays 54. The angle at which ray 54 impinges upon scale 50 are calculated with respect to the gemstone optical axis 24. Knowing the measurement of the angle of reflected light with respect to the gemstone optical axis, the calculation of the original angle at which the facet was cut can be calculated. The position of the facet around the gemstone 12 is determined by reading the setting of the index gear 34.

Figure 2:
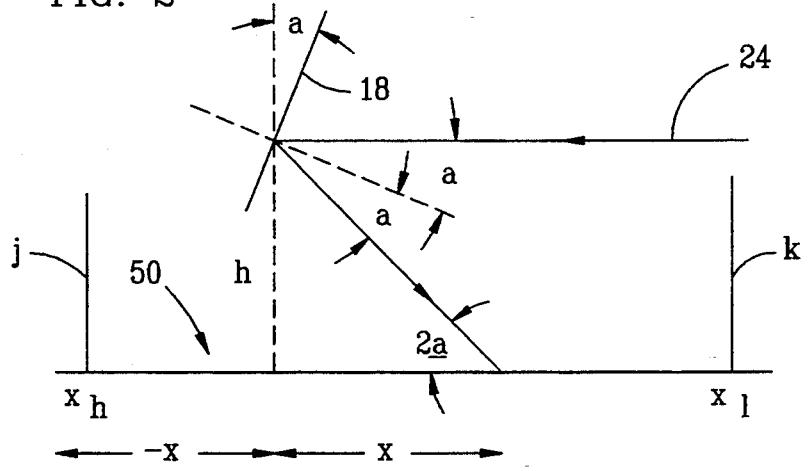
FIG. 2 illustrates a geometric diagram for use in determining the location of the indicia on the scale of the present invention.

The facet angle or indicia on scale 50 is described with respect to FIG. 2. Assuming, for example, that the optical axis is located at a distance of 76 millimeters from the scale 50, the location of indicia 52 is determined according to the following calculations:

$$\frac{h}{x} = \tan 2a \qquad (1)$$

$$\frac{x}{h} = \tan(90 - 2a) \qquad (2)$$

$$x = h \tan(90 - 2a) \qquad (3)$$

Where: h is the distance between the optical axis of the gemstone and scale 50;

a represents the angle of the selected indicia along scale 50; and x represents the location of the indicia for each selected angle.

Table 1 illustrates various angles and the dimension x in the positive direction. Table 2 illustrates various angles and the dimension −x in order to determine the location of the angular indicia on scale 50.

TABLE 1

| a° | x (m) |
|---|---|
| 45 | 0 |
| 40 | 13.40 |
| 30 | 43.88 |

TABLE 1-continued

| a° | x (m) |
|---|---|
| 20 | 90.57 |

TABLE 2

| a° | −x (mm) |
|---|---|
| 45 | −0 |
| 50 | −13.40 |
| 60 | −43.88 |
| 70 | −90.57 |

The reflected light in the form of rays 54 falls on scale 50 calibrated in the angles indicia 52 related to the facets 18 of gemstone 12. Each facet 18 is measured utilizing the present apparatus 10 by rotating gemstone 12 using facet machine 32 such that each facet can be measured without removing gemstone 12 from the present apparatus. Each facet of set 18 is measured individually through rotating index gear 34. Therefore, it is only necessary to mount gemstone 12 to apparatus 10 once in order to completely measure all facets of set 18.

Remounting the gemstone with the pavillion facing the light source and proceeding as discussed for the crown facets set 18, one measures the angles of pavillion set 20.

Since the tangent function of equation 3 extends from + infinity to − infinity as the angle a varies from 0° to 90°, a practical device would limit the range that angle a could be measured. This problem is avoided by placing the indicia on the vertical scale placed at some chosen distance $x_L$, FIG. 2, on the horizontal scale 50 for angle a approaching zero. The indicia on the vertical scale at a height k are given by $$k = (x - x_l) \tan 2a \quad (4)$$

where x is calculated by equation 3. A similar equation for j at a distance $x_l$ is used for angles approaching 90°.

It therefore can be seen that the present apparatus provides for a device and method for measuring the facets of a gemstone in an economical and accurate manner.

Wherein the present invention has been described with respect to specific embodiments thereof, it will be understood that various changes and modifications will be suggested to one skilled in the art and it is intended to encompass such changes and modifications as fall within the scope of the appended claims.

I claim:

1. A device for measuring the facet angle of a gemstone having an optical axis, the device comprising:
    means for rotatably mounting a gemstone along the optical axis of the gemstone;
    means for measuring the rotational location of a facet around the optical axis of the gemstone;
    means for generating a collimated beam of light directed toward a facet of the gemstone, such that the facet reflects a portion of said beam of light; and
    a scale mounted parallel to and spaced apart from the gemstone optical axis, said scale including indicia indicating angular measurements, such that said facet reflected light impinges on said scale, the location of said facet reflected light on said scale indicia indicating the angle of the facet with respect to the optical axis of the gemstone.

2. A method for measuring the facet angle of a gemstone having an optical axis, including the steps of:
    rotatably mounting a gemstone along the optical axis of the gemstone;
    measuring the rotational location of a facet around the optical axis of the gemstone;
    generating a collimated beam of light directed toward a facet of the gemstone, such that the facet reflects a portion of the beam of light; and
    providing a scale mounted parallel to and spaced apart from the gemstone optical axis, the scale including indicia indicating angular measurements, such that the facet reflected light impinges on the scale, the location of the facet reflected light on the scale indicia indicating the angle of the facet with respect to the optical axis of the gemstone.

* * * * *